United States Patent [19]

Coolidge et al.

[11] Patent Number: 5,464,759
[45] Date of Patent: Nov. 7, 1995

[54] SEQUENTIAL OLIGONUCLEOTIDE SYNTHESES USING IMMUNOAFFINITY TECHNIQUES

[75] Inventors: Thomas R. Coolidge, Falls Village, Conn.; William Lewis, Lincoln, Nebr.; Sheldon M. Schuster, Gainesville, Fla.; Jay Stout, Lincoln, Nebr.; Gino van Heeke, Gainesville, Fla.; Dwane Wylie, Lincoln, Nebr.; Fred W. Wagner, Walton, Nebr.

[73] Assignees: BioNebraska, Inc.; Board of Regents of the University of Nebraska, both of Lincoln, Nebr.

[21] Appl. No.: 18,100

[22] Filed: Feb. 17, 1993

Related U.S. Application Data

[60] Division of Ser. No. 454,372, Dec. 21, 1989, Pat. No. 5,221,736, which is a continuation-in-part of Ser. No. 288,009, Dec. 21, 1988, Pat. No. 5,049,656.

[51] Int. Cl.$^6$ .............................. C12P 19/34; C12Q 1/68
[52] U.S. Cl. ............................ 435/91.2; 435/6; 514/44; 536/22.1; 536/23.1; 536/24.1; 536/24.2; 536/24.31; 536/24.32; 536/25.3; 935/77; 935/78; 935/88
[58] Field of Search ........................... 435/6, 91, 91.2; 536/22.1, 23.1, 24.1, 24.2, 24.31, 24.32, 25.3; 935/78, 88, 77; 514/44

[56] References Cited

U.S. PATENT DOCUMENTS 4,689,405  8/1987  Frank ........................................ 536/27
4,711,955  12/1987  Ward et al. ............................... 536/29

FOREIGN PATENT DOCUMENTS 0196101  1/1986  European Pat. Off. .

OTHER PUBLICATIONS

J. W. Drijfhout et al., "Capping with o–Sulfobenzoic Acid Cyclic Anhydride (OSBA) in Solid–Phase Peptide Synthesis Enables Facile Product Purification," *Peptide Chemistry*, 1987:191–194 (1988).
R. A. Houghten et al., "The Rapid Preparation of Large Numbers of Discrete Peptides for Biological, Immunological, and Methodological Studies: Improved End–Capping Reagents," *Peptides 1988*, Proceedings of the 20th European Peptides Symposium held Sep. 4–9, 1988, pp. 214–216.
R. B. Merrifield, et al., "9–(2–sulfo) fluorenylmethyloxycarbonyl Chloride, a New Reagent for the Purification of Synthetic Peptides," *J. Org. Chem.* 43:4808–4809 (1978).
T. Weiland et al., "3–Nitrophthalic Anhydride as Blocking Agent in Merrifield Polypeptide Syntheses," *Angew. Chem. Internat. Edit.*, 8:764–765 (1969).
Dale et al. (1975) *Biochemistry*, vol. 14, No. 11, pp. 2447–2457.
Narang (1987) *Synthesis and Applications of DNA and RNA* (Academic Press Inc., N.Y., N.Y.) pp. 1–7.
*PCR Technology* (1989) (McMillan Publishers Ltd., England) pp. iii, ix, x, and 246.

*Applied Biosystems User Bulletin* 47, for Model 380B, entitled "RNA Synthesis" (Apr. 18, 1988).
*Applied Biosystems User Bulletin* 53, for Models 380A/380B/381A/391 EP DNA "Synthesizers, entitled RNA Synthesis with DMT–Cyanoethyl RNA Phosphoramidites" (Dec. 1, 1989).
S. Beaucage, "Deoxynucleoside Phosphoramidites—A New Class of Key Intermediates for Deoxypolynucleotide Synthesis", *Tetrahedron Letters*, 22:1859–1862 (1981).
E. R. Doran et al. "Purification of Synthetic Oligonucleotides", published by DuPont Central Research Development (published sometime before Dec. 1, 1988).
S. Marcus, "Agarose–Anthranilate Derivatives in the Purification of Anthranilate Phosphoriboxyltransferase", *Methods Enzymol.*, 34:377–385 (1974).
S. Narang in *Synthesis and Applications of DNA and RNA*, Academic Press, New York, at pp. 1–7 and 127–130 (1987).
*Science News*, 136:334, chapter entitled "Research Notes: Technology", article entitled Turning Plants Into Antibody Factories (Nov. 18, 1989).
W. Scouten, "Propyl Lipoamide Glass", *Methods Enzymol.*, 34:288–294 (1974).
Sigma Chemical Brochure entitled "Biochemicals Organic Compounds for Research and Diagnostic Reagents", published by Sigma Chemical Co., St. Louis, Mo., (1992).
O. Zaborsky, *Immobilized Enzymes*, CRC Press (1973) at pp. 5–48.
Stewart, *Solid Phase Peptide Synthesis*, second edition, Pierce Chemical Company, 41–42, published 1984.
Bodanszky, *Principles of Peptide Synthesis*, Springer–Verlag, 245, Published 1984.
Kohler et al., "Continuous cultures of fused cells secreting antibody of predefined specificity" *Nature*, vol. 256, 495–497, 1975.
Ikehara et al., "The Synthesis of Polynucleotides", *Advances in Carbohydrate Chemistry and Biochemistry*, 36, 135–213, Published 1979.
Ernst–Cabrera et al., "Immunoaffinity Chromatography and its application for the purification of pharmaceutically active proteins", *Medical Science Research*, 16, 305–310, Published 1988.
R. B. Merrifield, *J. Amer. Chem. Soc.*, 85, 2149–2154 (1963).
S. L. Beaucage and M. H. Caruthers, *Tet. Lett.*, 22, 1859–1862 (1981).

(List continued on next page.)

Primary Examiner—Margaret Parr
Assistant Examiner—Ardin H. Marschel
Attorney, Agent, or Firm—Merchant & Gould, Smith, Edell, Welter & Schmidt

[57] ABSTRACT

The invention is directed to a method of purifying sequentially synthesized peptides and oligonucleotides by affinity techniques. Selected products are capped with and N-terminus capping agent for peptides or a 5'-terminus capping agents for oligonucleotides, and then bound with affinity agents that are selective for the corresponding capping agents.

2 Claims, No Drawings

OTHER PUBLICATIONS

M. D. Matteuci and M. H. Caruthers, J. Amer. Chem. Soc. U, 103, 3185–3191 (1980).

L. D. Markley and L. C. Dorman, *Tet. Lett.*, 21, 1787–1790 (1970).

V. A. Efimov et al., *Nucleic Acids Res.*, 13, 3651–3666 (1985).

B. Penke and C. Birr, *Liebigs Ann. Chem.*, 1999–2002 (1974).

D. E. Krieger et al., *Proc. Nat'l Acad. Sci.*, 73, 3160–3164 (1976).

G. Baramy et al., *Int. J. Peptide Protein Res.*, 30, 705–739 (1987).

E. Engvall, *Methods In Enzymology*, 70, 419–439 (Academic Press, New York 1980).

W. D. Huse, et al., *Science*, 246, 1275–1281 (1989).

J. Coulter and R. Harris, *J. Immunol. Methods*, 59, 199–203 (1983).

J. Goding, *J. Immunol. Methods*, 20, 241–253 (1978).

J. Rousseaux, *J. Immunol. Methods*, 64, 141–146 (1983).

J. Goding, *J. Immunol. Methods*, 13, 215–226 (1976).

T. Tomono et al., *Biochem. Biophys. Acta*, 660, 186–192 (1981).

E. Ishikawa and S. Yoshitake, *J. Immunol. Methods*, 38, 117–123 (1980).

T. Kubiak et al., *Biochemistry*, 26, 7849–7855 (1987).

E. S. Ward et al., *Nature*, 341, 544–546 (1986).

A. Hiatt et al., *Nature*, 342, 76–78 (1989).

J. T. Johansen, *Carlsberg Res. Commun.*, 41, 73–80 (1976).

W. Scouten, *Methods Enzymol.* 34, 288–294 (1974).

S. Marcus, *Methods Enzymol*, 34, 377–385 (1974).

A. Matsura et al., *Methods Enzymol.*, 34, 303–304 (1974).

R. Barker et al., *Methods Enzymol.*, 34, 317–328 (1974).

I. Matsumoto et al., *Methods Enzymol.*, 34, 329–341 (1974).

J. Swack et al., *Anal. Biochem.*, 87, 114–126 (1978).

T. Updyke and G. Nicholson, *J. Immunol. Methods*, 73, 83–95 (1984).

S. G. Shoemaker, et al., *App. Biochem. Biotech.*, 15, 11–24 (1987).

R. T. Lee et al., *Anal. Biochem.*, 95, 260–269 (1979).

R. D. Guthrie et al., *J. Chem. Soc.*, C, 2690–2695 (1971).

N. Hsiung, et al., *J. Mol. Bio.*, 88 841–845 (1974).

R. E. Galardy et al., *J. Biol. Chem.*, 249, 3510–3518 (1974).

S. J. Jeng and R. J. Guillory, *J. Supramal. Struct.*, 3, 448–468 (1978).

S. H. Hixson and S. S. Hixson, *Biochemistry*, 14, 4251–4254 (1975).

J. C. Kauer et al., *J. Biol. Chem.*, 261, 10695–10700 (1986).

H. Eckert and C. Seidel, *Argew. Chem. Int. Ed. Engl.*, 25, 159–160 (1986).

A. J. Russel et al., *Biochem. Biophys. Res. Commun.*, 158, 80–85 (1989).

H. A. Erlich, et al., *PCR Technology*, (Stockton Press, New York, p. 246 1989).

U. Kasid et al., *Science*, 243, 1354–1356 (1989).

P. Cuatrecasas, *J. Biol. Chem.*, 245 3059–3065 (1970).

Biosearch Technical Bulletin No. 9000–01 (1988).

Biosearch Technical Bulletin No. 9000–03 (1988).

J. D. Haug, *Amer. Biotech. Lab.*, 40–47 (Jan./Feb. 1987).

C. Hoeger et al., *BioChromatography*, 2, 134–142 (1987).

M. Horn and C. Novak, *Amer. Biotech. Lab.*, (Sep./Oct. 1987).

M. P. Reddy and P. J. Voelker, *Int. J. Peptide Protein Res.*, 31, 345–348 (1988).

R. A. Houghton et al., *J. Peptide Protein Res.*, 27, 673–678 (1986).

R. A. Houghten et al., *BioTechniques*, 4, 522–528 (1986).

B. Merrifield, *Science*, 232, 341–347 (1986).

H. Seliger et al., *Tet. Lett.*, 24, 2115–2118 (1978).

J. P. Tam et al., *J. Am. Chem. Soc.*, 108, 5242–5251 (1986).

M. Wilcheck and T. Miron, *Peptides: Structure and Biological Function*, Proceedings of the Sixth American Peptide symposium, 49–57 (Pierce Publishing Co. 1979).

M. Wilchek and T. Miron, *Perspectives in Peptide Chemistry*, 185–194 (Karger Basel 1981).

J. I. Thornton, *Chem. & Eng. News*, 18–30 (Nov. 20, 1989).

C. Lichtenstein, *Nature*, 333, 801–802 (1988).

*Chem. & Eng. News*, 15–16 (D. O'Sullivan Nov. 20, 1989).

H. M. Weintraub, *Scientific Amer.*, 41–46 (Jan. 1990).

SEQUENTIAL OLIGONUCLEOTIDE SYNTHESES USING IMMUNOAFFINITY TECHNIQUES

This is a division, of application Ser. No. 07454,372, filed Dec. 21, 1989, now U.S. Pat. No. 5,221,736; which is a continuation-in-part of application Ser. No. 07/288,009 filed, Dec. 12, 1988, now U.S. Pat. No. 5,049,656.

BACKGROUND OF THE INVENTION

Sequential chemical peptide and: oligonucleotide syntheses are well established, widely used procedures for producing peptides and oligonucleotides, such as those up to and over about 100 residues (peptides) and up to and over about 200 residues (oligonucleotides). For peptides, the chemistry involves the specific coupling of the amino terminus of a carboxyl-blocked peptide to the activated carboxyl group of an amino-blocked amino acid. For oligonucleotides, the chemistry involves the specific coupling of the 5'-hydroxyl group of a 3'-blocked nucleotide to an activated 3'-hydroxyl group of a 5'-blocked nucleotide.

In their most commonly used forms, developed primarily by Merrifield, J,. Amer. Chem. Soc., 85, 2149 (1963) and Beaucage, S. L. and Caruthers, M. H., Tet. Lett., 22, 1859–1862 (1981); Beauoage, S. L. and Caruthers, M. H., J. Amer. Chem. Soc., 24, 3184–3191 (1981), these syntheses are accomplished with the peptide or oligonucleotide immobilized on a solid support. An extremely large number of peptides or oligonucleotides can be produced by this methodology. The physical and chemical properties of the peptide or oligonucleotide products will vary greatly depending on size and composition of the respective amino acids or nucleotides composing these products. Consequently, it is typical to tailor the synthetic techniques to fit the specific product at hand.

In the method of immobilized peptide synthesis, the carboxyl terminal amino acid is bound to a polyvinyl benzene or other suitable insoluble resin. The second amino acid to be added possesses blocking groups on its amino moiety and any side chain reactive groups so that only its carboxyl moiety can react. This carboxyl group is activated with a carbodiimide or other activating agent and then allowed to couple to the immobilized amino acid. After removal of the amino blocking groups the cycle is repeated for each amino acid in the sequence.

The efficiency of the peptide coupling step usually varies from 95–99.9%, depending on the identity of the amino acid and its location in the sequence. During each coupling step, a small portion of the peptides fail to couple the next amino acid. Since these failures occur independently during each coupling step, the amount of correctly sequenced peptide in the final mixture is often less than a major portion. Failed peptides with incorrect sequences (by virtue of amino acid deletions) often accumulate to a significant degree in this mixture.

The same is true of oligonucleotide syntheses. In general, the oligonucleotide synthetic procedure follows the well-established 3'-phosphoramidite schemes devised by Caruthers. The 3' terminal base of the desire oligonucleotide is immobilized on an insoluble carrier. The nucleotide base to be added is blocked at the 5' hydroxyl and activated at the 3' hydroxyl so as to cause coupling with the immobilized nucleotide base. Deblocking of the new immobilized nucleotide compound and repetition of the cycle will produce the desired final oligonucleotide.

As is true for the peptides, this nucleotide coupling procedure is not 100% efficient. The immobilized oligonucleotide molecules that do not couple result in oligonucleotides of incorrect sequences. These failed oligonucleotides often cause undesirable reactions if left in mixture with the correct oligonucleotide. Consequently, their separation and removal are mandated even though tedious procedures tailored to each specific synthesis are necessitated.

Separation of the various peptides or oligonucleotides in the respective mixtures produced during synthesis will produce the desired pure, correctly sequenced peptide or oligonucleotide. Conventional separation techniques usually employ high resolution chromatographic procedures such as reverse phase high pressure liquid chromatography, electrophoresis, gel chromatography and the like. These separation method(s) need to resolve peptides or oligonucleotides which differ from each other by as little as one amino acid or nucleotide. The failed peptides and oligonucleotides are compounds having physical and chemical properties very similar to the desired one. Consequently, the separations are difficult to accomplish. Since the compounds synthesized can vary greatly in composition, monomeric unit sequence and length, the separation methods also are individually tailored to the properties of each mixture. Such separation procedures are difficult to develop, require many man-hours to implement and do not insure absolute homogeneity of the product.

One means for attacking this problem involves increasing the coupling yield. This can be accomplished by performing repeated couplings at each coupling step prior to the next deblocking step. For example, for some residues, coupling is replicated three to four times at each coupling step just to get approximately 95% to 99.8% coupling. But repeated couplings provide only a partial solution to producing pure peptides or oligonucleotides. The repeated coupling steps expend larger quantities of expensive agents and protected amino acids or nucleotides. In manual synthesis, the coupling yield is monitored at each step before deciding whether to repeat the coupling step, whereas automated synthesis is severely restricted in this respect. Moreover, some peptides or oligonucleotides fail to couple completely during the chain elongation because the large size of the activated amino acid or nucleotide prevents access to some of the peptides or oligonucleotide molecules on the resin. Therefore, these methods are severely limited in scope.

Another means for attacking this problem involves "capping". This method reduces the total number of incorrectly sequenced or "failed" peptides or oligonucleotides in the synthetic mixture. To cap, the failed peptides or oligonucleotides are reacted with a capping agent which prevents the failed peptide or oligonucleotide from participating in subsequent coupling reactions (for peptides, see Merrifield, J. Amer. Chem. Soc. (1963) 2149; Markley and Dorman, Tetrahedron Letters, (1970), 1787; for oligonucleotides, see Efimov, V. A., Chakhmakhcheva, O. G., and Ovchimikov, V. A. Nucleic Acids Res. 13, 3651 (1985)).

As applied to peptides, capping can be accomplished because the extended (i.e., coupled) peptide possesses a blocked amino group at the N-terminus while the failed peptides possess a free N-terminus amino group. Once the failed peptide is capped, it is unavailable for further coupling steps. The result is a mixture of capped failed peptides of different lengths and the correctly extended peptide without a cap.

As applied to oligonucleotides, capping can be accomplished because the failed oligonucleotide contains a free 5'-hydroxyl group. Capping with an irreversible agent that reacts with hydroxyl groups will prevent further reaction of this failed side product. The cap will not react in any subsequent steps of the oligonucleotide synthetic procedure.

A modification of the capping strategy employs a capping agent which changes the chemical or physical properties of the failed peptides or oligonucleotides (Penke and Birr *Justis Liebigs Ann. Chem.*, 1999 (1974), and Krieger et al., *Proc. Nat. Acad. Sci.* 3160 (1976)). Such modifications augment the chemical and physical differences between the correctly extended peptide or oligonucleotide and the failed peptides or oligonucleotides. These differences tend to aid separation.

Nevertheless, these capping methods for reducing the contamination of synthetically produced peptides or oligonucleotides have drawbacks. No matter what the capping agent, the overall physical characteristics of the peptides or oligonucleotides usually determine their physical and chemical behavior. The resulting separations remain dependent upon the overall physical and chemical behavior of the peptides or oligonucleotides. Very tedious and time consuming separations result because the overall properties of the desired product and side products are much the same.

Therefore, it is an object of the invention to develop a synthetic method for the preparation of peptides and oligonucleotides that yields pure product. Another object is to develop a method that avoids time consuming separation techniques. Yet another object is to base this method upon a capping technique.

SUMMARY OF THE INVENTION

These and other objects are achieved by the present invention which is directed to a sequential peptide or oligonucleotide synthetic method that employs N-terminus or 5'-terminus capping agents respectively, and affinity agents that are selective for these capping agents.

According to one alternative for the method of the invention, failed peptides or oligonucleotides of the sequential synthesis are capped with an N-terminus or 5'-terminus capping agent. Specific affinity agents to these capping agents, which can be immobilized upon a solid support or may be in solution, bound with and remove the capped, failed peptides or oligonucleotides from the reaction mixture.

According to a second alternative for the method of the invention, the reverse capping procedure also allows isolation and purification of the desired peptide or oligonucleotide. Here, the desired, correctly sequenced peptide or oligonucleotide is capped as a last step of the synthetic sequence, while the failed peptides or oligonucleotides are capped with other reagents during each cycle of the synthetic sequence. Complexation with affinity agents selective for the capping agents on the desired peptides or oligonucleotides removes them from the reaction mixture. Dissociation of the complex then releases the desired peptides or oligonucleotides.

According to a third alternative for the method of the invention, double affinity separations can also be employed in which both the desired products and failed side products are capped and complexed with affinity agents. Differing caps for both the desired products and failed side products are introduced at the appropriate steps of the synthetic sequence. Affinity separation with two different affinity agents, which select for the desired and failed products, provides the separation of the desired product in an exceptionally high yield and efficient manner. Such double separations are particularly useful for purifying very long peptides or oligonucleotides from a large volume or concentration of improperly reacted side products with which they are mixed.

All embodiments of the method of the invention can employ the reverse capping procedure, can employ capping of failed peptides or oligonucleotides or can employ the double affinity separation.

According to the invention, various combinations of selective capping and affinity agents can be employed to isolate substantially pure polypeptides or oligonucleotides. For example, in one embodiment of the method of the invention, the capping agent is an antigen, and the affinity agent is an antibody that is selectively immunoreactive with the antigen cap. The antibodies employed in this embodiment can consist of monoclonal antibodies, polyclonal antibodies or antibody fragments of monoclonal or polyclonal antibodies. In addition, monospecific polyclonal antibodies, which are purified by utilization of an immobilized antigenic capping group, can be employed in the present invention.

In another embodiment of the method of the invention, the capping agent is an enzymatic substrate, inhibitor or cofactor, while the affinity agent is an enzyme that selectively binds with the enzymatic cap.

In another embodiment of the method of the invention, the capping agent is a ligand, such as a vitamin, sugar molecule or appropriate derivative, while the affinity agent is a ligand binding protein, such as an apoenzyme or lectin, that selectively binds with the ligand cap.

In another embodiment of the method of the invention, the capping agent is a covalent bond forming group, while the affinity agent is a covalent bond reactant that selectively reacts with the covalent bond forming cap. Such a covalent bond forming reaction can be accomplished by a thermal, polymerization or photolytic mechanism.

In a further embodiment of the method of the invention, the capping agent displays both affinity and photolabile properties. In this method, the bulk of the capped, unreacted peptide or oligonucleotide is first removed by binding the capped side products with an affinity agent (photochemical acceptor) that reacts with the photolabile portion of the capping agent. Then, in a second separation, the remainder of the capped unreacted side products are removed by binding with an affinity agent that binds with the ligand portion of the capping agent. This method provides an efficient means to purify large volumes of desired polypeptides or oligonucleotides.

According to the invention, a further embodiment of the method of the invention employs a capping agent that displays magnetic properties. The capped, unreacted peptide, or in the reverse capping procedure, the desired, capped polypeptide, is isolated by passing the mixture of capped and uncapped products by a magnet that attracts and holds the capped products, thereby isolating the desired polypeptide. Various ferrocene derivatives can serve as the magnetic capping agent.

According to another embodiment of the invention, the cap-affinity agent separation method can facilely practiced by employing chaotropic agents, such as urea and guanidine hydrochloride, to unfold the secondary and tertiary structure of the unreacted peptides or oligonucleotides; and/or organic solvents, such as dimethyl sulfoxide (DMSO) dimethyl formamide (DMF) and the like, to solubilize the unreacted peptides or oligonucleotides. The increased solubility or unfolded structure of the peptides. or oligonucleotides exposes the capped terminus to bind with the appropriate affinity agent. Such a system provides for increased purification of the larger synthesized polypeptides and oligonucleotides, by solubilizing or uncovering the capped terminus which often becomes buried in the secondary and tertiary structure of the polypeptide or oligonucleotide.

According to the invention, the specific affinity agents may be immobilized upon a solid support or they may be maintained in solution during the cap-affinity agent complexing process. Separation in the former situation may be accomplished by removing the uncapped products. In the latter, it may be accomplished by taking advantage of a unique chemical or physical property of the complexed product.

The invention is also directed to an agent kit containing the capping agent, the affinity agent in appropriate buffers and agents for utilization in a sequential peptide or oligonucleotide synthesis.

In addition, the invention also encompasses methods of providing substantially pure polypeptides and oligonucleotides for use in PCR (Polymerase Chain Reaction) technology and antisense RNA and DNA diagnosis and treatment of diseases, genetic disorders and other special applications.

DETAILED DESCRIPTION OF THE INVENTION

Chemically synthesized peptides of up to and over about 15 thousand molecular weight and pieces of single stranded DNA of 20 to over 200 bases have a variety of commercial, experimental, medical and diagnostic uses. In the research environment, peptides and oligonucleotides can be used as probes and reagents. For example, a DNA probe for isolating DNA fragments from nuclear material has great utility in the field of recombinant DNA technology. Synthetic DNA can also be used as a clinical diagnostic probe for specific viruses or cells. Peptides or oligonucleotides labeled with fluorescent probes also have utility as therapeutic agents to detect diseases, foreign bodies and genetic disorders. Aspharmaceuticals, peptides control physiological processes and hence are of great value in the treatment of disease and injury. But the presence of failed peptides or oligonucleotides in mixture with the desired ones may result in toxic, antigenic, unknown or undesirable activities. Consequently, there is a great need to prepare such peptides and oligonucleotides in substantially pure form.

Nevertheless, one of the key draw-backs of synthetic peptide or oligonucleotide production is the seemingly difficult task of purification of the final product. Currently, high performance liquid chromatography (HPLC) procedures are employed. These procedures are not readily adaptable to large samples and are not completely effective in removing all contaminants from a sample. The present invention addresses and solves these difficulties.

The method of the present invention is a purification procedure based upon selective interaction between a capping agent and an affinity agent. It involves capping those selected peptides or oligonucleotides, or a synthetic mixture, that are to be removed by binding with an affinity agent that is selective for the cap on the peptides or oligonucleotides.

In one version of the method, those selected compounds have failed to incorporate the amino acid or nucleotide unit being coupled during a cycle of a sequential synthesis. Here, the capped peptides or oligonucleotides constitute impurities in the mixture and are easily removed by binding with the affinity agents according to the invention. By this means of purification, the correctly synthesized, uncapped peptide or oligonucleotide is obtained in purified form.

In a second version of the method, those selected compounds are the reverse of the failed peptides or oligonucleotides. Here, only the desired product (peptide or oligonucleotide) is selectively capped while the failed side products are capped with other reagents that do not bind under the specific conditions of the affinity technique being employed.

In a third version of the method, both the desired polypeptides or oligonucleotides and the failed side products are capped with capping agents that will bind and/or react with affinity agents. Double separation is accomplished by sequential treatment, in any order, with the affinity agent for the capped desired products and the capped failed side products. Of course, the two capping and affinity agent pairs employed will differ so that cross-binding or chemical reactivity between, for example, the affinity agent for the capped desired product and the cap of the capped failed side product does not occur. This double separation method allows for the purification of very long sequence peptides and oligonucleotides, including oligonucleotides of over 200 base pairs, in a very high yield and efficient manner, that previously were very difficult to separate from a large volume and/or concentration of improperly sequenced side products.

The purification steps of the method are dependent on the specificity of the affinity agent for the capping group and are independent of both the chemical and the physical characteristics of the peptides or oligonucleotides. The failed peptides or oligonucleotides, or, for the reverse procedure, the desired ones, are removed by a single affinity reaction respectively that is common to all failed peptides or oligonucleotides regardless of their sequence, or, for the reverse procedure, that is unique to the desired peptide or oligonucleotide. Hence, a simple, single purification is made and the final product will not contain any peptides or oligonucleotides containing failed sequences.

I. Capping/Affinity Agent Systems

A. Antigen/Antibody Systems

According to one embodiment of the method of the invention, the capping agent employed to cap selected peptides or oligonucleotides is an antigen, and the affinity agent is an antibody that is selectively immunoreactive with the antigenic cap. Binding of the antigenically capped peptide or oligonucleotide with the corresponding antibody, either in solution or on a solid support, allows for purification of the desired polypeptide or oligonucleotide.

1. Antigenic Peptide Capping Agents

According to the invention, the agent for capping failed peptides is designed so that specific antibodies toward the capping group (monoclonal,-polyclonal or fragments of monoclonal or polyclonal antibodies) can be produced. The peptide capping agent is generally an aromatic acylating agent that is reactive toward free amino groups of peptides and is capable of causing an immune response either alone or when reacted with a carrier protein to form a hapten. Especially preferred peptide capping agents are fluorescamine and its derivatives, and substituted or unsubstituted compounds of phthalic anhydride, benzoyl halide or naphthoyl halide wherein the substituents are mono-, di- or tri-cyano; mono-, di- or tri-carboxy; mono-, di- or tri-nitro; or mono-azido; and the halide is fluoride, chloride, bromide or iodide including dinitrobenzoyl chloride (DNB) or 3-nitrophthalic anhydride (NPA). These agents produce the acylated derivatives of the targeted peptides in the reaction mixture. The acylation terminates any further reaction of the failed peptides in subsequent coupling reactions.

The failed peptide capping agent in general has several properties. It is highly reactive toward amino groups and is small enough to have access to the resin bound peptide. These features insure that all of the failed peptides are capped. The capping agent is also antigenic so that antibodies may be produced which bind the capped peptides. To insure that the correctly synthesized, uncapped peptide is not bound by the antibodies to the capping group, the capping group is not antigenically similar to any of the functional groups normally found in peptides. Further properties include capping group stability under the conditions for synthesis of the peptide and for removal of the protective groups attached to the peptide during synthesis. Finally, the capping agent is inexpensive. This expediently enables use of large excesses of the agent and insures complete reaction.

Generally, the peptide synthetic sequence practiced during the performance of the invention follows well-known procedures for peptide-peptide coupling and peptide functional group protection. See, for example, George Barany, et al., *Intl. J. Peptide Protein Res.*, 30, 705–739 (1987), the disclosure of which is incorporated herein by reference. Foresight shows that reactions to remove these protecting and blocking groups should not also remove the capping agent. Consequently, the protective and blocking groups are chosen so that they can be removed in the presence of a stabilized capping agent. Examples of such protecting and blocking groups include aromatic sulfonyl groups, benzyl groups, pyridyl sulfenyl groups, benzyloxymethyl groups, and alkyloxycarbonyl groups, as well as others listed at Table 1 of the Barany article.

During this synthesis, the correctly formed peptides are not derivatized by the capping agent since the amino group of these peptides possesses any of the well-known blocking groups. After the completion of the synthetic sequence, the correct peptide and all the capped failed peptides are deprotected by standard procedures. The capping groups on the failed peptides are not removed by these methods. The result is a mixture of peptides in which all peptides, except the correctly synthesized sequence, are present as the capped derivatives.

This mixture of peptides is preferably combined with an immunoaffinity resin containing immobilized antibodies (monoclonal or polyclonal or antibody fragments of monoclonal or polyclonal antibodies) against the cap functional group. The capped peptides are specifically bound to this resin while the correctly synthesized peptide remains unbound. The solution containing the correctly formed peptide is separated from the resin containing the failed peptides or peptides of incorrect sequence.

The reverse capping procedure calls for antigenically capping the correctly sequenced peptide. Here, the usual N-block, C-block and pendant functional group protecting agents that can be removed with HF, acid hydrolysis or other non-basic techniques form the basis for the usual synthetic sequence manipulations. Reversible amine peptide capping groups including aromatic sulfinyl groups, such as 9(2-sulfo)-fluorenylmethyloxycarbonyl (SULFmoc), fluorenylmethyloxycarbonyl (Fmoc) or trinitrobenzene sulfonyl chloride (TNB), and aryloxy carbonyl groups, such as carbobenzoxy chloride (CBZ), that. are removable by base or catalytic hydrogenation treatment constitute the antigenic capping agents for the amino terminus of the desired peptide. These capping agents can be added to the desired peptide as the amino protecting group of the N-terminal amino acid. These capping agents are stable to the normal N-block deprotection procedures, i.e., HF, but are easily removed by aqueous alkali or catalytic reduction. The immunoaffinity techniques employing antibodies to these groups then will be directed to the desired peptide, while the failed peptides that are capped with other reagents are washed away or otherwise removed.

2. Antigenic Oligonucleotide Capping Agents

The agents for capping failed and desired oligonucleotides are designed so that specific antibodies toward them (monoclonal, polyclonal or antibody fragments of monoclonal or polyclonal antibodies) can be produced. The capping agent is generally an acylating, phosphorylating or carbamylating agent that is reactive toward free 5'-hydroxyl groups of failed oligonucleotides and is capable of causing an immune response either alone or when reacted with a carrier. Especially preferred oligonucleotide capping agents are substituted or unsubstituted aromatic isocyanates, dialkoxytriazoylphosphine, dialkyl or diaryl phosphoramidites, aliphatic acid halides of 2 to 10 carbons and substituted or unsubstituted compounds of phthalic anhydride, benzoyl halide or naphthoyl halide wherein the substituents are mono-, di- or tri-nitro; mono-, di or trialkoxy; mono-, di- or tri-cyano; mono-, di- or tricarboxyl; or mono-azido; and the halide is fluoride, chloride, bromide or iodide.

The capping agent allows purification of the desired oligonucleotide from all the undesired oligonucleotides. As this technique is applied to both versions of the method of the invention, monoclonal, polyclonal antibodies or antibody fragments of monoclonal or polyclonal antibodies to the capping agent or to the standard 5' blocking group are generated. In the first instance, immunoaffinity binding will bind the failed oligonucleotide to the immunoaffinity support. In the second, (the reverse procedure) the desired oligonucleotide will be bound.

In general, the capping agent for failed oligonucleotides has several properties. It is highly reactive toward hydroxyl groups and is small enough to have access to the resin bound oligonucleotide. These features insure that all of the failed oligonucleotides are capped. The capping agent is also antigenic so that antibodies may be produced which bind the capped oligonucleotides. To insure that the correctly synthesized, uncapped oligonucleotide is not bound by the antibodies to the capping group, the capping group is not antigenically similar to any of the functional groups normally found in oligonucleotides. Further properties include capping group stability under the conditions for synthesis of the oligonucleotide and for removal of the protective groups attached to the oligonucleotide during synthesis. Finally, the capping agent is inexpensive. This expediently enables use of large excesses of the agent and insures complete reaction.

Generally, the oligonucleotide sequential synthesis practiced in accordance with the invention follows the well-known techniques laid out by Caruthers, cited above and reviewed by S. A. Narang, in *Synthesis and Applications of DNA and RNA*, Academic Press, New York, 1987, the disclosure of which is incorporated herein by reference. Appropriate 3'- and 5'-hydroxy protecting and activating groups as well as pendant function group protective agents are incorporated in this synthesis with the synthetic logic expressed by those in the art, such as Narang.

Within the oligonucleotide synthesis and purification, according to the invention, the immunoaffinity technique requires only one separation step. Where the immunoaffinity separation is directed toward the failed oligonucleotide, the antigenic capping agent characterized above is reacted with the failed oligonucleotide at the end of the synthetic cycle and before the 5'-blocking group is removed. Selection of the appropriate capping agent will take into account the needed differing reactivities of the capping, protecting and blocking groups. Removal of one or more, but not all, of these groups pursuant to the logic of the synthetic sequence guides this selection. Especially preferred capping agents for failed oligonucleotides include 3-nitrophthalic anhydride (NPA), aromatic isocyanates and aromatic acylating groups.

Where the immunoaffinity separation is directed toward the correctly sequenced oligonucleotide, a standard 5'-capping group, such as acetic anhydride or another acylating group caps the failed oligonucleotides pursuant to known procedures (See, e.g., Narang cited above). The correctly sequenced oligonucleotide will be capped with a dimethyltrityl (DMT), dansyl or other ether 5'-blocking group as mentioned above. The only oligonucleotide designed to bind with the antibodies will be the correctly sequenced one. Thus, this procedure is applicable to any automated synthetic solid-phase oligonucleotide synthesis procedure.

3. Antibody Affinity Agents

According to the invention, the specific antibodies employed are monoclonal antibodies, polyclonal antibodies and fragments of monoclonal and polyclonal antibodies including but not limited to Fab, F(ab)$_2$, light or heavy chains, light or heavy chain fragments, recombinant variable region fragments or dabs antibody fragments. Preparation and purification of these antibodies is described below.

a. preparation of Polyclonal Antibodies

Polyclonal antibodies to the antigenic capping agent, e.g. the dinitrobenzoyl (DNB) group, are prepared by injecting a capped hapten carrier such as capped Keyhole Limpet Hemocyanin (KLH) or capped Bovine Serum Albumin (BSA) (e.g. a hapten carrier such as KLH that has been reacted with a capping agent such as DNB to form a capcarrier such as DNB-KLH) into animals such as rabbits, goats, sheep, horses, donkeys and chickens. The capping agent is coupled to the hapten carrier, such as KLH, under the usual protein acylating conditions. After animal serum antibody titer is maximal (6–8 weeks), the IgG fraction is purified from the blood serum by precipitation, such as by use of ammonium sulfate at 33–45% of saturation. The anticap antibodies (i.e. those that complex with cap) are further purified by immunoaffinity chromatography against one or more immobilized cap carriers. For example, purification on DNB-diethylamine-Sepharose against immobilized cap-KLH, then against immobilized cap-Bovine serum albumin (BSA coupled with the capping agent) is an appropriate method. Antibodies which bind to cap-KLH and cap-BSA are selected for use.

b. Preparation of Monoclonal Antibodies

Alternatively, monoclonal antibodies can be used; however, in this case monoclonal antibodies may be specific for particular capped amino acids. Thus, clones of monoclonal antibodies must be screened with all 20 capped amino acids as well as any modified amino acids or amino acid analogues used for particular applications. All 20 amino acids plus any analogues or modified amino acids used for the synthesis of the peptide must bind to the antibody or a mixture of antibodies selected for use.

For preparation of monoclonal antibodies to nucleotides and for each of the agents to be used as immunizing agents, there will be 4 possible nucleotide derivatives to which monoclonal antibodies with be synthesized. Thus in each instance it will be necessary to immunize separate mice with, for example, 5'-dimethoxytrityl (DMT) or 5'-cap derivatives of each of the four 2-deoxyribonucleotides found in DNA, namely, adenine, guanosine, cytosine and thymidine, or screen the antibody against the capped derivatives of each nucleotide.

The antigenic capping agent is covalently bound to a hapten carrier such as keyhole limpet hemocyanin (KLH) or Bovine Serum Albumin (BSA). The suspension is used to immunize a host animal such as a mouse, preferably by injection. The laboratory strain of mouse designated BALB/c is particularly preferred.

Antibody-producing cells of the immunized host are collected by removing the host's spleen and preparing a suspension of spleen cells. The spleen cells are fused with cells of a myeloma cell line, preferably of the same animal species as the immunized host, and typically in the presence of a cell fusion promoter such as polyethylene glycol to form hybridoma cells. The hybridoma cells are diluted and cultured in a medium which does not promote the growth of unfused cells.

The monoclonal antibodies produced and secreted by the hybridomas are thereafter assayed for the ability to bind immunologically with the capping agent used for immunization. The preferred assay method in this context is an enzyme-linked immunoabsorbent assay. See, for example, E. Engvall, *Methods In Enzymology*, Vol. 70, p. 419–438, Academic Press, New York 1980 for a general discussion of the enzyme-linked immunoabsorbent assay, the disclosure of which is incorporated herein by reference. Screening for the hybridomas will be performed with capping agent bound to each of the 20 amino acids or 4 nucleotides so that antibodies selected bind only to the capping agent regardless of which amino acid or nucleotide residue constitutes the site for attachment of the capping agent.

Another alternative method for generating the monoclonal antibodies used in the invention is based upon the cloning method of W. Huse et al., *Science*, 246, 1275–1281 (1989), the disclosure of which is herein incorporated by reference, in which a recombinant vector such as a recombinant bacteriophage lambda vector system is used to express in an appropriate organism, such as *Escherichia coli*, a combinatorial library of Fab fragments or the intact antibodies of the mouse antibody repertoire, followed by selection for the desired monoclonal antibody.

c. Preparation of Fragments of Monoclonal and Polyclonal Antibodies

As a further alternative, fragments of monoclonal or polyclonal antibodies can be utilized in the present invention. Advantageously, antibody fragments retain the immunospecificity of the complete antibody at a fraction of their size. Thus, when utilized in the immunoaffinity reaction of the present invention, a much higher concentration of these fragments can be immobilized on the same volume of an affinity column, resulting in increased binding capacity of the affinity column. The method of Huse et al., supra, as well as various other methods for generating these antibody fragments are described below.

1) Preparation of Fab or F(ab)$_2$ Antibody Fragments

Monoclonal or polyclonal antibodies to antigenic capping agents, such as dinitrobenzoyl (DNB), are prepared as described in sections 3 a) and b) above. Fab or F(ab)$_2$ antibody fragments are then prepared as follows.

Preparation of Fab antibody fragment is described in J. Coulter and R. Hanis, *J. Immunol. Methods.*, 59, 199–203 (1983); J. Goding, *J. Immunol. Methods*, 20, 241–253 (1978) and J. Rousseaux, *J. Immunol. Methods*, 64, 141–146 (1983) the disclosures of which are herein incorporated by reference. Briefly, the lyophylized monoclonal or polyclonal antibodies are digested with an immobilized protease, such as papain, followed by chromatographic separation with, for example, immobilized Protein A.

An example of this procedure is as follows. Up to 10 mg of monoclonal or polyclonal antibodies, or 20 mg/ml of an antibody solution can be dissolved into the digestion buffer provided in Pierce Kits. Immobilized papain is equilibrated with digestion buffer and resuspended digestion buffer in a test tube. The antibody sample solution can be added to the equilibrated immobilized papain in the test tube. The resulting mixture can be incubated in a shaker water bath. The crude digested product can be separated from the immobilized papain using a separator tube. The immobilized papain is washed with binding buffer, and the wash solution is added to the crude digested product. An immobilized Protein A column is equilibrated with binding buffer and the crude digested solution can be applied to the column. The Protein A column is washed with binding buffer and the eluate is collected. The eluate will contain the Fab fragments.

F(ab)$_2$ antibody fragments are prepared by a methodology described in J. Goding, *J. Immunol. Methods*, 13, 215–226 (1976), T. Tomono et al., *Biochem. Biophys. Acta*, 660, 186–192 (1981) and E. Ishikawa and S. Yoshitake, *J. Immunol. Methods*, 8, 117–123 (1980), the disclosures of which are herein incorporated by reference. Briefly, the monoclonal or polyclonal antibodies are digested with a protease that cleaves a specific amino acid sequence or cleaves amino acid sequences in certain conformations.

An example of this general procedure is as follows. A volume of immobilized pepsin (prewashed in buffer) is added to antibody in sodium acetate buffer at pH 4.5. This solution can be incubated with rocking. Then, Tris-HCl can be added to the solution, resulting in a pH of 7.5. The resulting solution can be mixed and centrifuged. The resulting supernatant can be applied to an Immobilized. Protein A column, which is previously equilibrated with Tris-HCl pH 7.5. The column can be washed with Tris buffer, pH 7.5. The protein eluted will be the F(ab)$_2$ antibody fragment.

2) Seguencing and Synthesis of Antibody Fragments

According to the invention, an alternative method of obtaining antibody fragments involves determining the sequence of the variable domain of an antibody, and chemically synthesizing a peptide corresponding to that sequence. The method employed is similar to that utilized by T. Kubiak et al., *J. Am. Chem. Soc.*, 26, 7849–7855 (1987), the disclosure of which is herein incorporated by reference, in which the heavy chain hypervariable region of a differentiated antibody such as the phosphocholine binding IgA M603 was synthesized by a solid-phase fragment strategy. This peptide was then recombined with the natural light chain in order to obtain a functional antibody binding site.

3) Random Method for Antibody Generation

According to the invention, a further alternative method of obtaining antibody fragments is patterned after the random antibody generation of W. Huse et al., supra, the disclosure of which is incorporated herein by reference. Briefly, both hypervariable regions of the light and heavy chains of the antibody are cloned into the same vector after they have been separately digested with restriction enzymes, which act like the immune system in the mouse, to generate a random sequence for the binding site of each chain. This allows a large number of recombinant antibodies to be produced and screened and a greater number of clones to be obtained. These recombinant antibodies can then be produced in large quantities by various methods, including transfection of eukaryotic organisms, such as plants and insects.

4) Preparation of Mini dabs Antibody Fragments

According to the invention, a further alternative method of obtaining antibody fragments involves recovering genetic material that encodes for the immunospecific heavy-chain variable domain of an antibody and replicating the fragments in a bacteria, such as *Escherichia coli*, to produce mini "dAbs" antibodies. The specific method of generating dabs antibody fragments appears in E. Ward et al., *Nature*, 341, 544–546 (1986), the disclosure of which is herein incorporated by reference. Briefly, mice are immunized either with lysozyme or keyhole-limpet hemocyanin (KLH). DNA is recovered from the spleens of the of the sensitized mice and the specific genetic material that encodes for the lysozyme or KLH antibody fragments is harvested using the polymerase chain reaction technique, and cloned. The cloned fragments are introduced into *E. coli* bacteria through various vectors. The transformed bacteria express the dabs. The dabs produced by the bacteria pass through the cell walls into the supernatant solution, and are recovered and purified.

The specificity and affinity of the variable domain dabs antibody fragments produced lies within the range expected for analogous monoclonal antibodies generated against the same protein antigen. Antibody fragments produced by the above methodology are much cheaper than analogous monoclonal antibodies. In addition, these antibody fragments can potentially be produced by transformed eukaryotic organisms, such as plants and insects, thereby opening up the possibility of low-cost, large scale production of dabs antibody fragments. See A. Hiatt et al., *Nature*, 342, 76–78 (1989), the disclosure of which is herein incorporated by reference.

B. Enzymatic Affinity Systems

According to another embodiment of the method of the present invention, the capping agent for selected peptides or oligonucleotides is an enzymatic substrate, inhibitor or cofactor, while the corresponding affinity agent is an enzyme that selectively binds with these capping agents. Binding of the capped peptide or oligonucleotide with the corresponding enzyme affinity agent allows for purification of the desired peptide or oligonucleotide.

According to the invention, an enzymatic capping agent is selected that preferentially binds with an enzyme to be employed as an affinity agent. The selected capping agent will display the same desirable characteristics with respect to reactivity, stability and selectivity towards amino and 5'-hydroxyl groups that was described for the antigenic peptide and oligonucleotide capping agents respectively. Especially preferred combinations of enzymatic capping agents and affinity enzymes include aromatic and heteroaromatic sulfanilamide or sulfanilic acid derivatives with human carbonic anhydrase B and C (See J. Johansen, *Carlsberg Res. Commun.*, 41, 73–80 (1976), the disclosure of which is herein incorporated by reference), lipoic acid and its derivatives with dihydrolipoyl transacetylase or lipoamidase (See W. Scouten, *Methods Enzymol.*, 34,288–294 (1974), the disclosure of which is herein incorporated by reference), and anthranilic acid and its derivatives with anthranilate synthetase (See S. Marcus, *Methods Enzymol.*, 34, 377–385 (1974), the disclosure of which is herein incorporated by reference).

In Johansen, a methodology is described for isolating human carbonic anhydrase B and C by affinity chromatography employing sulfanilamide inhibitors coupled to the column resin. Such a methodology is adaptable to the present invention through utilization of sulfanilamide and its derivatives as capping agents which allow the capped peptides and oligonucleotides to be purified on an affinity column composed of human carbonic anhydrase B or C bound to a particulate carbohydrate such as sepharose. Briefly, the enzyme inhibitor is converted to a highly reactive form, such as an acyl chloride of sulfanilic acid, for use as a capping agent. Once capped, the peptide serves as a functional inhibitor of carbonic anhydrase B and C. The carbonic anhydrase enzyme, which serves as the affinity agent, is then bound to an immobilized protein on a solid support, by conventional technology, such as the use of carbonyl diamidazole to couple proteins to carbohydrate particulates. Thereafter, the capped peptide is applied to the affinity column containing the immobilized carbonic anhydrase. The capped peptide selectively binds to the active site of the immobilized carbonic anhydrase, and only the uncapped peptide elutes from the carbohydrate gel. Examples of such ligand cap and enzyme affinity agent pairs include anthranilic acid and anthranilate synthetase, lipoic acid and dihydrolipoyl transacetylase or lipoamidase.

C. Ligand/Protein Affinity Systems

According to another embodiment of the method of the invention, the capping agent for selected peptides or oligonucleotides is a ligand, such as a vitamin or sugar molecule, while the corresponding affinity agent is the corresponding ligand binding protein, such as an apoenzyme or lectin. Binding the ligand capped peptide or oligonucleotide with the corresponding affinity agent allows for purification of the desired peptide or oligonucleotide.

According to the invention, a liganous capping agent, such as a vitamin or sugar molecule, is selected which preferentially binds to a ligand binding protein, such as an apoenzyme or lectin, which serves as the affinity agent. The selected capping agent will display the same desirable characteristics with respect to reactivity, stability and selectivity towards amino and 5-hydroxyl groups that was described for the antigenic peptide and oligonucleotide capping agents respectively. Especially preferred combinations of capping and affinity agents are described below.

1. Vitamin/Apoenzyme Systems

Vitamin and apoenzymes pairs can be utilized according to the general scheme of the invention described above. The vitamins can be bound to the peptide or oligonucleotide through standard techniques such as acyl halide reaction with amine or hydroxy groups, diimide or azole coupling and ketal or ether bond formation through condensation techniques. The apoenzymes can be immobilized as described above for the enzymes. Examples of the pairs include NAD with a protein alcohol dehydrogenase, pyrazol derivatives with an alcohol dehydrogenase, riboflavin with a glucose oxidase, lipoic acid with a lipamide dehydrogenase, and t-Boc capped thiamine pyrophosphate and its derivatives which form phosphoesters with the oligonucleotides or phosphoamides with peptides. This final t-Boc capping group will react with immobilized thiamine-binding protein from *E. coli* (See A. Matsura et al., *Methods Enzymol.*, 34, 303–304 (1974), the disclosure of which is herein incorporated by reference).

2. Sugar Molecules and Lectin

Various sugar molecules and lectin pairs can be utilized according to the general scheme of the invention described above. The sugars can be bound to the peptide or oligonucleotide through standard techniques such as acetal or ketal formation, epoxy condensation and ether bond formation through condensation techniques. The lectin can be immobilized as described above for the enzymes. Examples of the pairs include, 3,4,6-tri-O-acetyl 6-carboxy- 1-hexyl-2-acetamido-2-deoxy-β-D-glycopyranoside, 3,4,6-tri-O-acetyl-N-(6-carboxyhexoyl)-β-D-galactopyranosylamine or 3,4,6-tri-O-acetyl-N-(6-carboxyhexoyl)-β-D-glucosamine and derivatives with garden pea, wheat germ or lima bean lectin respectively (See R. Barker et al., *Methods Enzymol.*, 34,317–328 (1974) and I. Matsumoto et al., *Methods Enzymol.*, 34, 329–341 (1974), the disclosures of which are herein incorporated by reference, and additional references cited in these publications).

3. Biotin and Avidin/Strepavidin

Biotin and avidin or strepavidin pairs can be utilized according to the general scheme of the invention described above. The biotin and avidin/strepavidin can be bound to the respective peptide/oligonucleotide/particulate material according to the techniques described above for enzymes/vitamins/enzyme substrates. Examples include, biotinoyl chloride and other activated biotin derivatives which can be used as the capping agent, and which can be applied on either an avidin or strepavidin Sepharose column. The avidin and strepavidin can also be bound to porous glass beads (See J. Swack et al., *Anal. Biochem.*, 87, 114–126 (1978) and T. Updyke and G. Nicholson, *J. Immunol. Methods*, 73, 83–95 (1984), the disclosure of which are herein incorporated by reference).

D. Covalent Bonding Affinity Systems

According to another embodiment of the method of the present invention, the capping agent for selected peptides or oligonucleotides is a covalent bond forming agent, while the complimentary affinity agent is a covalent bond reactant that selectively reacts with the capping agent by a thermal, polymerization or photolytic reaction. Binding the covalent bond forming, capped peptide or oligonucleotide with the corresponding affinity agent allows for purification of the desired peptide or oligonucleotide.

According to the invention, an covalent bond capping agent is selected that preferentially binds with a covalent bond reactant to be employed as an affinity agent. The selected capping agent will display the same desirable characteristics with respect to reactivity, stability and selectivity towards amino and 5'-hydroxyl groups that was described for the antigenic peptide and oligonucleotide capping agents respectively. Several different preferred reactants and mechanisms can be utilized to accomplish the affinity coupling of the above method.

1. Acrylic Acid Systems

In one embodiment of the above method, an acrylic acid or related derivative is employed as the capping agent. The acid is coupled to the selected peptide or oligonucleotide through an acid chloride or anhydride reaction. Thereafter, the capped, selected products are removed by either a Dieis-Alder reaction in which the solid support in the purification carries a diene, such as maleic anhydride, or by the addition of a radical initiating reagent, such as ammonium persulfate in the presence of acrylamide or a solid support containing a double bond which will result in the formation of a polymer containing the failed peptide or oligonucleotide (See S. Shoemaker et al., *Appl. Biochem. Biotech.*, 15, 11–24 (1987); R. Lee et al., *Anal. Biochem.*, 95, 260–269 (1979), the disclosures of which are herein incorporated by reference).

2. p-vinybenzoic Acid Systems

In another embodiment of the above method a p-vinylbenzoic acid derivative is employed as the capping agent. Following free radical initiation, the p-vinylbenzoic acid will react with styrene. Thus, the peptide or oligonucleotide sample may be dissolved in a solution containing styrene, and mildly polymerized by addition of a free initiator such as m-chloro-perbenzoic acid to form a copolymer containing the capped, selected peptides or oligonucleotides. Separation of the copolymer from the solution will produce the purified desired peptide or oligonucleotide (See R. Guthrie et al., *J. Chem. Soc., C*, 2690–2695 (1971), the disclosure of which is herein incorporated by reference).

3. Photolytic Systems

In a final embodiment of the above method, a photolabile group, such as p-benzophenonyl-L-phenylalanine, p-azidobenzoic acid, p-azidobenzoyl chloride, pazidobenzoylglycine, 3-azido-5-nitrobenzoic acid, 3-azido-5-nitrobenzoylglycine and aromatic azido compounds containing carboxylic acid side chains (See N. Hsiung et al., *J. Mol. Biol.*, 88, 841–845 (1974); R. Galardy et al., *J. Biol. Chem.*, 249, 3510–3515 (1974); S. Jeng and R. Guillory, *J. Supramol. Struct.*, 448–456 (1975); S. H. Hixson and S. S. Hixson, *Biochemistry*, 14., 1140123 (1975), the disclosures of which are herein incorporated by reference), are employed as the capping agent. When exposed to a predetermined wave length of light, the photoreactive capping agent will react with a selective affinity agent, thus providing a means of isolating selected peptides and oligonucleotides.

The use of p-benzophenonyl-L-phenylalanine (Bpa) as a photoreactive amino acid analog, and its subsequent incorporation into synthetic peptides has been described by J. Kauer et al., *J. Biol. Chem.*, 261, 10695–10700 (1986), the disclosure of which is herein incorporated by reference. Briefly, Bpa was incorporated into a 17-residue calmodulin binding peptide by Merrifield solid phase synthesis. The Bpa incorporating peptide was cleaved from. the resin by reaction with HF/p-cresol(10:1) at 0° C. for 60 minutes. The crude product was then purified in a single step by reversed-phase HPLC. Fractions containing pure peptide were pooled and lyophilized to yield a homogenous peptide product.

According to the invention, such a photolabile peptide could be employed as a capping agent for utilization in subsequent purification of desired peptides or oligonucleotides. In addition to p-benzophenonyl-L-phenylalanine, other potential photolabile capping agents include the N-hydroxysuccinate ester of N-ethyl-maleimide and the m-maleimidobenzoyl-N-hydroxysulfoxysuccinimide ester or heterobifunctional groups which contain the photoreactive group aryl azides, such as p-azidobenzoic acid, p-azidobenzoyl chloride, p-azidobenzoylglycine, 3-azido- 5-nitrobenzoic acid, 3-azido-5-nitrobenzoylglycine and aromatic azido compounds containing carboxylic acid side chains.

E. Magnetic Affinity Systems

According to. a further embodiment of the method of the present invention, the selected peptides are capped with an agent that displays magnetic properties, such as ferrocene derivatives. After attachment of the magnetic capping agent, the selected peptides are isolated by passing the mixture of desired and unreacted peptides by a magnet that selectively attracts and holds the capped peptides. Thereafter, the magnetic cap, when employed on the desired peptide can be removed by reduction of the iron group. The magnetic capping agent will display the same desirable characteristics with respect to reactivity, stability and selectivity towards amino groups that was described for the antigenic peptide capping agents.

1. Synthesis of Magnetic Capping Agent

The synthesis of ferrocenyl methyl (Fem)-amino acid derivatives, and their incorporation into peptides is described in H. Eckert and C. Seidel, *Angew. Chem. Int. Ed. Engl.*, 25, 159–160 (1986), the disclosure of which is herein incorporated by reference. Briefly, a mixture consisting of an amino acid ester or its hydrochloride, a ferrocenylmethyl (Fem) group derivative such as ferrocenyl aidehyde, and palladium phthalimide in methanol and ethyl acetate can be saturated with $H_2$ and vigorously stirred under $H_2$ for several hours until gas absorption stops. The reaction mixture can be filtered through a layer of $Na_2SO_4$ washed with ethyl acetate, and the filtrate can be concentrated. The residue can be chromatographed on silica gel with hexane/ethyl acetate, resulting in the Fem-amino acid ester. This Fem-amino acid ester may be incorporated. into a peptide by combination with a N-urethane-protected amino acid, by cooling in dichloromethane. A solution of dicyclohexyl carbodiimide in dichloromethane can be added and the cold bath removed. After a time the dicyclohexylurea is filtered off, and the filtrate concentrated. The residue can be chromatographed on silca gel with hexane/ethyl acetate, which will produce the Fem-substituted peptide.

F. Dual Affinity Systems

According to a further embodiment of the method of the present invention, the capping agent for the selected peptides or oligonucleotides displays both affinity and photolabile properties. Thus, a capping agent, such as a derivative of p-benzophenonyl-L-phenylalanine (Bpa), which will insert into carbon-hydrogen bonds through a photolytic reaction, can be utilized to remove the bulk of the capped, selected peptides from the reaction mixture through a photolytic reaction with an insoluble matrix at a predetermined wavelength of light. The small percentage of capped peptide that remains in the mixture can be removed through an selective reaction between an affinity agent and the ligand portion of the capping agent. Additional examples of capping agents displaying photolabile properties include the photoreactive group aryl azides, such as p-azidobenzoic acid, p-azidobenzoyl chloride, p-azidobenzoylglycine, 3-azido-5-nitrobenzoic acid, 3-azido-5-nitrobenzoylglycine and aromatic azido compounds containing carboxylic acid side chains, as well as the N-hydroxysuccinate ester of N-ethyl-maleimide and the m-maleimidobenzoyl-N-hydroxysulfoxysuccinimide ester.

G. Affinity Systems in Organic Solvents or Chaotropic Solutions

In a further embodiment of the method of the present invention, the affinity re! actions between the capping agents and corresponding affinity agents can be run in solutions of organic anhydrous solvents or chaotropic solutions (salt solutions that disrupt hydrogen bond formation). Such a modification of any of the above methodologies is particularly useful when dealing with large sequenced peptides or oligonucleotides which are especially insoluble or possess a great deal of secondary or tertiary structure. Thus, the capping group is often buried in the secondary and tertiary structure, and therefore is unavailable for complexing with an affinity agent. By running the affinity reactions in organic solvents, thereby solubilizing the insoluble peptides or oligonucleotides, or in chaotropic solutions, thereby unfolding the secondary and tertiary structure of the peptides or oligonucleotides, the capped termini of these peptides or oligonucleotides are rendered available for binding with their corresponding affinity agents. Especially preferred organic solvents include dimethyl formamide, dimethyl sulfoxide, dioxin (DMSO), acetonitrile, ethanol, methanol acetone, dimethylglycol and methylethylglycol, while preferred chaotropic solutions include mixtures containing urea, guanidine hydrochloride and formamide.

H. Double Separation Affinity Systems

In a further embodiment of the method of the present invention, both the desired peptides or oligonucleotides, and the side products generated during their synthesis, are capped with capping agents that are selective for different affinity agents. Thus, for example, an antigenic capping agent that immunospecificly binds with a first antibody affinity agent may be employed to cap the desired peptides or oligonucleotides, while the improperly sequenced side products can be capped with an enzymatic substrate, inhibitor or cofactor capping agent that selectively binds to an enzyme affinity agent, or with a second antigenic cap that selectively binds with a second antibody affinity agent but not with the first antibody affinity agent. Such a double separation affinity system is particularly useful for purifying very long sequenced peptides or oligonucleotides, including oligonucleotides of over 200 base pairs in length. Accordingly, the mixture of capped desired peptides or oligonucleotides is first applied to an affinity column that selectively binds, and thereby removes, a large percentage of the capped side products. Thereafter, the remaining mixture is applied to an affinity column that selectively binds the capped desired products, thereby efficiently isolating substantially pure peptides or oligonucleotides.

1. Antigen/Antibody Systems. Employing Organic Solvents or Chaotropic Solutions

Generally, the modified procedure for isolating capped, selected peptides and oligonucleotides in organic solvents or chaotropic solutions may be described with reference to antigen/antibody affinity systems described in section A above. See A. Russell et al., *Biochem. Biophys. Res. Commun.*, 158, 80–85 (1989), the disclosure of which is herein incorporated by reference. Briefly, the capped peptide or oligonucleotide is unfolded in a chaotropic solution containing urea (8M) or guanidine hydrochloride (6M). Then,-the affinity column is conditioned with urea (8M) or guanidine hydrochloride (6M), which initially denatures the antibody. However, the chaotropic solution concentration to be used in the column is then diluted to a point sufficient to reactivate the antibody, but retain the capped peptides or oligonucleotides in solution. Thereafter, the solubilized and denatured peptides or oligonucleotides are eluted on the antibody affinity column, thereby isolating the desired peptides or oligonucleotides.

Anhydrous organic solvents such as dimethyl sulfoxide, dimethyl formamide, tetrahydrofuran and glyme can be used in place of aqueous system to dissolve the products and side products and perform the separation.

In addition to the antigen/antibody systems, the other embodiments described in the present invention will also function in anhydrous organic solvents or in chaotropic solutions.

II. Preferred Methods of Application

The high purity polypeptides and oligonucleotides produced according to the method of the present invention are useful in applications which rely upon such compounds as intermediates and/or final products for biological, veterinary and/or medical diagnostic, treatment or analytic purposes, for research and development purposes, or for industrial purposes such as quality control, fermentation use, .biological processing control and recombinant technology. Applications requiring large quantities of homogenous peptides and oligonucleotides are also well suited for use of the methods of the invention. A particular example is the amplification of RNA and DNA and in the detection and treatment of various diseases and genetic disorders. The PCR (Polymerase Chain Reaction) technology employs oligonucleotide primers in the amplification of DNA segments. The DNA diagnostic probes produced by this technology are utilized to detect infectious disease pathogens and in the identification of genetic variation associated with monogenic, and mutagenic disease. However, the widespread application of this technology has been hampered by the difficulty in obtaining large quantities of substantially pure oligonucleotide primers. The method of the present invention overcomes this deficiency.

The basic methodology, research and medical applications of PCR technology are described in H. A. Erlich, ed., *PCR Technology*, Stockton Press, New York, pp. 246 (1989), the disclosure of which is herein incorporated by reference. Briefly, PCR is an in vitro method for the enzymatic synthesis of specific DNA sequences, using two oligonucleotide primers that hybridize to opposite strands and flank the region of interest in the targeted DNA. A repetitive cycling of template denaturation, primer annealing, and the extension of the annealed primers by DNA polymerase results in the exponential accumulation of the specific DNA segment sought. Because the primer extension products synthesized in one cycle can serve as the template for the next cycle, the number of DNA segment copies approximately doubles at each cycle. Thus, PCR can yield a million fold amplification in approximately 20 cycles. See Erlich, supra.

Another use of the high purity polypeptides and oligonucleotides of the present invention is in the generation of antisense RNA and DNA for use in the diagnosis and therapeutic treatment of diseases and genetic disorders. See U. Kasid et al., *Science.*, 243, 1354–1356 (1989), the disclosure of which is herein incorporated by reference. For example, the method of the present invention may be utilized to synthesize a complimentary strand of RNA oligonucleotide, which will bind to, and inhibit the expression of an endogenous oncogene. Thus, in cancer therapy, a resistent tumor could be rendered more susceptible to chemotherapeutic or radiation treatment.

III. General Techniques

A. Capping of Failed Peptides

The synthesis of the peptides is accomplished by conventional synthetic sequence methods using known N- and C-blocking and activating agents respectively such as t-BOC and FMOC; carbodimide, or acyl halide and symmetric anhydrides. Preferably, peptide synthesis occurs on a solid support. The capping of the peptides which do not couple the added amino acid at each step requires additional steps to be added to each synthetic cycle. Following the reaction of the activated amino acid with the immobilized peptide, the resulting product mixture is reacted with a capping agent of the particular methodology being employed. The capping agent reacts with the remaining $NH_2$ groups to form a nonreactive, irreversible derivative of the failed peptides. The agents are removed. and the t-BOC protecting groups on the remaining peptides are removed as in the usual methodology.

B. Capping of Desired Peptide

Subsequent to the practice of the foregoing failed peptide capping procedure, the desired peptide is capped with an affinity capping agent that does not de-cap under usual acidic deblocking and deprotecting conditions but will under basic conditions.

C. Capping of Failed Nucleotides

The syntheses of the oligonucleotides is accomplished by conventional synthetic sequence methods including binding on a solid support. The capping of failed oligonucleotide that does not couple with the added activated nucleotide also requires an additional step. Following the reaction of the 3'-activated, 5'-blocked nucleotide with the immobilized deprotected oligonucleotide, the product mixture is reacted with a capping agent of the selected methodology. The capping agent readily combines with the 5'-hydroxyl groups of the unreacted, immobilized oligonucleotide. Oxidization of the phosphite group of the capped nucleotide produces a phosphate group. The resulting capped side product is stable to the remainder of the reaction sequence.

D. Capping of Desired Oligonucleotides

In the reverse procedure, the failed oligonucleotides can also be capped with a capping agent. The final step of the synthesis generates a 5' standard blocking group (e.g. with trityl or dansyl) upon the correctly sequenced oligonucleotide which distinguishes it from the 5'-capped, failed oligonucleotide.

E. Affinity Chromatography of Peptides or Oligonucleotides

The affinity agents are immobilized to a resin by conventional methods. See for example Cuatrecasas, *J. Biol. Chem.*, 245, 3059 (1970.) the disclosure of which is incorporated herein by reference. Briefly, the affinity agents in buffered aqueous solution are mixed with an activated resin to form covalent bonds or strong complexes between the agent and resin. Typical covalent activating agents for the resin include cyanogen bromide, N-hydroxysuccinimide, carbonyl diimidazole and toluene sulfonyl chloride as well as others discussed by Cuatrecasas. Typical resins include Sepharose (a modified polydextran made by Pharmacia Inc., Sweden), agarose, polyacrylamide, cellulose, porous glass beads and other carbohydrate derived resins. The covalent activating agents are reacted with the resin to form links for covalent attachment of the affinity agents to the resin. Strongly complexing resins such as ion exchange resins can also be used.

The affinity agent resin is then used to remove the capped peptides or nucleotides from the peptide or oligonucleotide mixture. The lyophilized mixture, containing the capped peptides or oligonucleotides (failed or desired) and the remaining peptides or oligonucleotides, is dissolved in a buffer solution (pH 6.5–8.0). The affinity resin is equilibrated in the same buffer and packed into a conventional chromatography column. The sample is added to the column and the column is washed with buffer until the major peptide or oligonucleotide band is eluted. The capped peptides or oligonucleotides remain bound to the resin and can be eluted by washing the resin in a buffered solution at pH 9.5–10.5. The affinity resin can be reused by extensive washing in the original buffer.

The column effluent is monitored continuously at either 220 nm or 260 nm wavelengths where peptides and nucleotides possess high molar absorptivities, respectively.

F. Separation of Complexed Affinity Products

As an alternative to immobilized affinity separation, the specific affinity agents in media can be added to the appropriate capped mixture of materials. Precipitation of the cap-affinity agent complex with complement or with base or acid buffer will then remove the capped materials. Other known methods for separation of media borne cap-affinity agent complexes include physiochemical separations including magnetic systems, phase partitioning especially by chromatography, particle exclusion filtration, sedimentation and dialysis.

The utility of the methods of the present invention is conferred by a combination of the addition of a capping group to the failed or desired peptides or oligonucleotides and the use of an affinity resin directed specifically toward the capping group for separation of these peptides or oligonucleotides.

These components are described in the following examples which illustrate the application of the method in both manual and automated synthetic protocols. The examples are intended as illustrations only and is not meant to limit the invention thereto.

In the examples, acronyms are given for solvents and agents. The full name is given the first time a particular solvent or agent is indicated.

EXAMPLE 1

Peptide Synthesis

Leu-enkephylin, a peptide hormone produced by the pituitary gland, was synthesized by standard manual methods and by the same method modified to include the present invention. The sequence of leu-enkephalin is Tyr-Gly-Gly-Phe-Leu.

Manual Synthesis of Leu-Enkephalin

Synthesis of leu-enkephylin by the conventional methods involved the following steps:

1) The starting resin, N-tBOC-Leucyl polystyrene is placed in the reaction vessel.
2) The resin is washed with dry dichloromethane (DCM).
3) The tBOC protecting group is removed by incubating the resin in 10 ml of 20% triflouroacetic acid (TFA) in DCM for 28 minutes.
4) The resin is washed in DCM, then in 5% triethylamine in DCM.
5) The resin is suspended in 10 ml DCM.

6) A five-fold excess of the next amino acid, N-tBOC-Phe, is added to the resin along with an equimolar amount (relative to amino acid) of dicyclohexylcarbodiimide.

7) The mixture is incubated for 45 minutes at room temperature.

8) Steps 2–6 are repeated for each amino acid in the sequence substituting the appropriately blocked amino acid in step 6. The amino acids used are:
cycle 2; N-tBOC-Gly
cycle 3; N-tBOC-Gly
cycle 4;O-(2-Br-OZ-N-tBOC-Tyr)

9) The resin is washed with DCM.

10) 1.5 ml of 2:1 thioanisole: ethanedithiol (EDT) is added to the resin.

11) The mixture is stirred for 10 minutes.

12) One ml of TFA is added and the mixture was stirred for 10 minutes.

13) 100 ml of trifluoromethanesulfonic Acid (TFMSA) is slowly added.

14) The mixture is stirred for 1 hour at room temperature.

15) The mixture is filtered through a sintered glass funnel into 25 ml of methyl t-butyl ether.

16) The reaction vial is washed 3 times with 0.5 ml TFA. The wash solution is filtered through the sintered glass funnel and collected as in step 14.

17) The combined filtrates are incubated at 4° for 15 minutes.

18) The precipitated peptide is collected by filtration through a clean sintered glass funnel and washed with methyl t-butyl ether.

19) The peptide is dissolved in 0.1% TFA and lyophylized.

20) The peptide is washed by three cycles of suspension in water and then dried by lyophylized.

Manual Synthesis of DNB-capped Leu-Enkephalin

The twenty step procedure given above was followed to synthesize the DNB capped peptide except that the following modifications were made.

Following the procedure described in step 7, the following steps are added in each cycle.
i) The resin is washed with DMF.
ii) The resin is incubated with a tenfold excess of dinitrobenzoyl chloride (relative to the peptide) in DMF.
iii) The resin is washed with DMF.

The DNB capping group is not removed by this procedure.

EXAMPLE 2

Bradykinin, a vasoactive peptide secreted by the liver, was synthesized by using a Dupont Coupler 2200 automated synthesizer using the protocol supplied by the manufacturer and the same method modified to incorporate the present invention. The protocols used are summarized below and along with the modifications made to incorporate the capping steps. The sequence of bradykinin is Arg-Pro-Pro-Gly-Phe-Ser-Pro-Phe-Arg.

Automated Synthesis of Bradykinin

1) The resin, N-tBOC-arginyl-phenylacetoamidomethyl-polystyrene (PAM) is placed in the reaction vessel.

2) The resin is washed with 60% TFA in DCM.

3) The t-BOC protecting group is removed by incubation of the resin with 10 ml of 60% TFA in DCM for 15 minutes.

4) The resin is washed three times with 10 ml of DCM.

5) The resin is washed twice with 10 ml of 10% diisopropylethylamine.

6) The resin is washed 3 times with 10 ml DMF.

7) The second amino acid, N-tBOC-Phe, is dissolved in DMF.

8) The amino acid is activated and attached to the resin-bound peptide according to the Instrument manufacturer's protocol. This protocol varies, depending on the identity of the amino acid. Activation is accomplished by incubation with diisopropylcarbodiimide and hydroxybutyltriazole in DMF.

9) Following the coupling, the resin is washed with 7 ml DMF.

10) Steps 3–9 are repeated for each amino acid in the sequence. The protected amino acids used in step 7 for subsequent cycles of the bradykinin synthesis are:
cycle 2; N-tBOC-Pro
cycle 3; O-Benzyl-N-tBoc-Ser
cycle 4; N-tBOC-Phe
cycle 5; N-tBOC-Gly
cycle 6; N-tBOC-Pro
cycle 7; N-tBOC-Pro
cycle 8; tosyl-N-tBOC-Arg 11) After the synthesis is complete the resin is incubated at 0° C. with freshly distilled HF, containing 10% thioanisole, to remove the peptide from the resin and remove all blocking groups.

12) Residual HF is removed from the product by vacuum distillation. The peptide is precipitated with diethyl-ether and extracted into 10% acetic acid. The acetic acid is removed by sublimation to yield the crude peptide powder.

Automated Synthesis of DNB,Capped Bradykinin

1) The synthesis of the capped peptide follows the procedure for the uncapped peptide except that the following steps are added in each synthetic cycle following step 8.
i) The resin is washed three times with 10 ml DMF.
ii) The resin is incubated with 10% DNBCL IN DMF at room temperature for 20 minutes.

2) The DNB capping group is not removed by HF deblocking in step 11.

Affinity Chromatography of Peptides

The peptides produced are all subjected to immunoaffinity chromatography on a column containing the immunoaffinity resin. The antibody used was a polyclonal anti-DNB antibody produced in a rabbit. The resin used was cyanogen bromide treated Sepharose gel brand of modified polydextran (Pharmacia, Sweden). The following steps were applied to the purification of each peptide.

1) The resin is packed into a chromatography column.

2) The column is equilibrated with an 0.1M solution of $K_2HPO_4$ buffer (pH 7).

3) The peptide mixture is dissolved in the same buffer.

4) The peptide solution is applied to the column.

5) The column is eluted with the buffer.
6) The effluent is monitored at 210 nm.
7) The major absorbing peak is collected.
5 8) The column is regenerated by Washing with 0.1M sodium carbonate, 8M urea or combinations of the two, followed by extensive washing in the pH 7 buffer.
9) The peptide solution collected is lyophylized to yield the purified peptide.

EXAMPLE 3

General Procedure for Preparation of Oligonucleotide

1. Hydroxyl (3') attachment to the insoluble support.

The 5' DMT blocked nucleoside desired to be at the 3' terminus of the synthetic oligonucleotide is attached to controlled pore glass by a spacer arm. Resins, containing each of the four possible nucleosides, can be purchased commercially.

2. Removal of the immobile 5-DMT group.

Generally 5% dichloroacetic acid in dichloromethane is used to hydrolyze the DMT group from the 5'-terminus of the growing oligonucleotide.

3. Chain elongation.

In this step a 3'-activated 5'-DMT blocked nucleotide is allowed to react with the immobile free 5'-group of the growing oligonucleotide. The 3' activation group is 3'-(beta)-cyanoethylphosphoramidite. This step is usually 98% complete; however, the 2% that does not react will be available for reaction in the next cycle and will produce an oligonucleotide with a base deleted from the desired sequence. At this point in the synthesis these free 5' hydroxyls of the 2% failed oligonucleotide are "capped" with an acylating agent.

4. Capping.

At this point, the capping method can be used to generate an antigenic capped oligonucleotide. The capping agent is an acylating agent such as 0.25M 3-nitrophthalic anhydride in acetonitrile and activated with an equal volume of a separate catalyst solution of 10% triethylamine and 10% N-methylimidazole in acetonitrile. The capped oligonucleotide will consequently possess an 3-nitrophthalic group instead of an acetyl group. These capped sequences are no longer available for chain elongation.

5. Oxidation.

The phosphite group of the nucleotide is oxidized to a phosphate group with iodine.

6. Further chain elongation by repeating steps 2 through 5.

7. Deprotection and cleavage.

The solid phase oligonucleotide is incubated in concentrated ammonium hydroxide during which time it is cleaved from the resin by base hydrolysis. This step also facilitates the removal of the cyanoethyl protecting groups from the phosphate groups.

8. Removal of base protecting groups.

The bases adenine guanosine and cytosine are protected with benzoyl groups (A and C) or isobutyryl groups (G). These groups removed by further reaction the oligonucleotide in concentrated ammonium hydroxide for 12 hr. at 55° C.

Purification of Capped Oligonucleotides

The soluble oligonucleotide possessing the DMT blocking groups (as well as those blocking groups removed in step 8) are eluted through an immunoaffinity resin. The resin possesses immobilized antibodies to either the DMT group or to the NPA (3-nitrophthalic group). In the former case the desired 5' blocked oligonucleotide will adhere to the resin and all the undesired capped oligonucleotides will elute. The DMT oligonucleotide can be eluted from the resin by conventional procedures, or the resin can be treated with acid as in Step 2 to cleave the DMT from the oligonucleotide where upon the latter will elute form the affinity column.

If the oligonucleotide has been capped with NPA then the product from Step 7 or Step 8 is passed over an immunoaffinity column containing bound antibody to NPA. Under these conditions all capped oligonucleotides will bind to the column and the desired product will elute. The column can be washed with dilute acid or base to elute the NPA capped oligonucleotides.

Separation of Oligonucleotides by Immunoaffinity Chromatography

Lyophylized synthetic oligonucleotides are dissolved in phosphate buffered saline, pH 7.0 (PBS). The antibody column is also equilibrated in PBS buffer. The sample is added to the column, then the column is washed with PBS. If the immunoaffinity support is specific for DMT the major DMT-oligonucleotide will remain bound to the resin and the capped oligonucleotides which do not contain DMT will elute. The DMT-oligonucleotide can be eluted as described for the NPA resin or the column can be eluted with acid as in Step 2 of the procedure hydrolyze DMT from oligonucleotide, thus releasing it from the resin.

Palindromic Oligonucleotide Synthesis

Following the foregoing procedure, a palindromic 18 nucleotide long oligonucleotide is synthesized using a Vega Coder 300 automated synthesizer. The sequence of the oligonucleotide is 5' GAATTCGGATCCGAATTC 3'. This sequence has two EcoR1 sites at either end and a BamH1 site in the middle.

Synthesis of 18 nucleotide long oligonucleotide convention methods involved the following steps:

1. The 5' dimethoxytrityl (DMT) blocked benzyl-cytosine-B-cyanoethyl phosphoramidite at the 3' terminus was purchased in a form that was already attached to controlled pore glass by a spacer arm.
2. The DMT protecting group was removed from the 5' hydroxyl group by 5% dichloroacetic acid in dichloromethene.
3. The 150 uL of 5' DMT thymidine-B-cyanoethyl phosphoramidate was then mixed with 150 uL of tetrazole. The coupling reaction was then allowed to occur for 3 minutes.
4. The 5' hydroxyl groups of unreacted cytosine were then capped with 150 uL of acetic anhydride and 150 uL of n-methylimidazole. The capping reaction was complete in 30 seconds.
5. The 3-' phosphite formed is then oxidized to the phosphate by the reaction with an iodine solution for 30 seconds.
6. The steps 2–5 are repeated for each nucleotide in the sequence substituting the appropriately blocked amino acid in step 3. The nucleotides used are:
   cycle 2; 5'-O-DMT-T-B-cyanoethyl phosphor-amidite (DMT-T)
   cycle 3; 5'-O-DMT-Adenosine-B-cyanoethyl phosphoramidite (DMT-A)
   cycle 4; DMT-A cycle 5; 5'O-DMT-1Bu-dG-B-cyanoethyl phosphoramidiite (DMT-G)
cycle 6; 5'O-DMT-Bz-dC-B-cyanoethyl phosphoramidite (DMT-C)
cycle 7; DMT-C
cycle 8; DMT-T
cycle 9; DMT-A
cycle 10; DMT-G
cycle 11; DMT-G
cycle 12; DMT-C
cycle 13; DMT-T
cycle 14; DMT-T
cycle 15; DMT-A
cycle 16; DMT-A
cycle 17; DMT-G 7. The resin is reacted with concentrated ammonium hydroxide at 50° C. for 16 hours.
8. Vortex sample and allow resin to settle.
9. Decant liquid from resin.
10. Vacuum centrifuge to dryness.

A Palindromic Synthesis of NPA-capped Oligonucleotide

The procedure described above is repeated with the following modifications:

1. The acetic anhydride in step 4 is replaced by a solution of 3-nitrophthalic anhydride (NPA) in acetonitrile and activated with an equal volume of a separate catalyst solution of 10% triethylamine and 10% N-methylimidazole in acetonitrile.
2. After step 6 for cycle 17 step 2 is included.

The mixture of NPA capped palindromic failed oligonucleotides and the correctly sequenced palindrome can then be chromatographed on an immunoaffinity column of rabbit anti-NPA antibody coupled to Sepharose brand of modified polydextran as described above for peptide chromatography. Elution with appropriate buffer yields the desired product.

EXAMPLE 4

Synthesis of GTP-binding fragment of the sequence NH$_2$-Glu-Glu-Glu-Met-Leu-Pro-Gly-Asp-Leu-Ser-COOH way performed on a Milligen 9050 Synthesizer using a 0.099 mmole scale, Ser bound resin and an 8 fold excess of amino acid. The coupling reaction was on an instrument 30 minute coupling cycle with capping. The coupling protocol was modified to include a capping step of 20 minutes followed by a 10 minute wash with DMF. The reagent in bottle four was replaced by a solution of 0.1M dinitrobenzoyl chloride in DMF.

The synthesis required 13 hours and 33 seconds for completion and consumed 963 mls of DMF, 189 ml of piperidine, 0 mls of DCM, 540 mls of 0.1M DNBCl in bottle 4, 26 mls of HOBt reagent and 0 mls of SP3.

The resin was washed with piperidine following the last synthetic cycle. The resin was then washed with DMF for 10 minutes and DCM for 15 minutes, and dried in vacuo overnight.

The peptidyl-resin was cleaned and deprotected with 95% TFA/5% H$_2$O for four hours, after which the TFA solution was removed and saved. The resin was then washed 3 times with 5 mls of the TFA solution. All solutions were pooled and dried in vacuo.

The residual peptide was dissolved in 10 mls of distilled H$_2$O and then freeze dried.

The freeze dried peptide was diluted to 1 mg/ml and a 1 ml solution was eluted onto a 5 ml anti-DNB antibody column. The antibody was bound to Sepharose CL-4B after the Sepharose had been activated with caronyldiimidazole.

Freeze dried peptide was dissolved to 1 mg/ml and a 1 ml solution eluted on a 5 ml carbonyldiimidazole activated Sepharose column.

The column was washed with phosphate buffered saline (PBS) and fractions collected. The desired peptide was eluted with this buffer.

EXAMPLE 5

Synthesis of the following synthetic oligonucleotides was performed on a Vega Coder model 300:

1) CTCTCTCTCT     10mer

2) GTCTATCGGCTCCTGCTTCTGAGAGGA     29mer

3) GGTTTTCCAGTCACGACGGCCTTCCTACAAGGGAAGGCC

Synthesis of the above oligonucleotides, utilizing a 1.0 µmole scale column, dT, dA, dC respectively and a ten fold excess of nucleotide phosphoramidite, was performed. The instruments software was not modified. The capping reagent solution, 0.25M 3-nitrophthalic anhydride in acetonitrile, and activated with an equal volume of a separate catalyst solution of 10% triethylamine and 10% N-methylimidazole in acetonitrile, was used to replace the acetic anhydride reagent.

The oligonucleotides were cleaved from the controlled pore glass bead by reaction with 30% NH$_4$OH in H$_2$O for 30 minutes at room temperature.

The NH$_4$OH was removed in vacuo.

The residual oligonucleotides were separated from the controlled pore glass beads by dissolving in distilled H$_2$O.

The solution was then eluted on a 5 ml column of carbonyldiimidazole activated Sepharose with attached anti-NPA antibodies. The antibodies bound at 5 mg/ml.

The column was eluted with PBS, and desired oligonucleotides were eluted off the column while the capped oligonucleotides were retained.

The desired oligonucleotides were then deprotected in 1 ml of 30% NH$_4$OH at 55° C. for 15 hours.

What is claimed is:

1. A method for DNA replication comprising: applying to the DNA to be replicated, a polymerase chain reaction technique in combination with an oligonucleotide probe produced by a method comprising:
    (a) preparing a 3'-blocked nucleotide compound of at least one nucleotide in length;
    (b) reacting a 3'-activated, 5'-blocked nucleotide with the 3'-blocked nucleotide compound to produce a mixture of an extended nucleotide compound and an unreacted nucleotide compound;

(c) adding a 5'-terminus capping agent to the mixture to cap the unreacted nucleotide compound;

(d) combining the mixture of the extended nucleotide compound and the 5'-capped unreacted nucleotide compound with an affinity agent that is selective for the cap on the 5'-capped. unreacted nucleotide; and (e) isolating the extended nucleotide compound thereby producing the oligonucleotide.

2. The method of claim 1 wherein the replicated DNA is further used in a diagnostic for a genetic disorder in a human or an animal.

* * * * *